United States Patent [19]

Kirk et al.

[11] 4,163,450

[45] Aug. 7, 1979

[54] METHOD AND APPARATUS FOR WEANING PATIENT FROM CONTINUOUS MECHANICAL VENTILATION

[76] Inventors: Bryan W. Kirk, 229 Lamont Blvd.;
Monte B. Raber, 83 Coralberry Ave.;
Donald J. Hatch, 91 Brian St.;
Harvey E. Cramp, 122 Balfour Ave.,
all of Winnipeg, Canada

[21] Appl. No.: 762,990

[22] Filed: Jan. 27, 1977

[51] Int. Cl.[2] ............................................. A61M 16/00
[52] U.S. Cl. .................................................. 128/145.8
[58] Field of Search ......................... 128/145.5–145.8, 128/188, 202

[56] References Cited

U.S. PATENT DOCUMENTS

| | | | |
|---|---|---|---|
| 3,951,143 | 4/1976 | Kitrilakis et al. | 128/145.8 |
| 3,967,619 | 7/1976 | Story et al. | 128/145.8 |
| 3,976,064 | 8/1976 | Wood et al. | 128/145.8 |
| 4,003,377 | 1/1977 | Dahl | 128/145.8 |

*Primary Examiner*—Henry J. Recla
*Attorney, Agent, or Firm*—Stanley G. Ade

[57] ABSTRACT

A continuous mechanical ventilator system includes a ventilator known in the art, with a pneumatic circuit connectable to the patient and operating in the normal manner. A bag and bag valve are interposed within the pneumatic connection such that when the value is closed, the patient is on full assisted breathing from the ventilator. When the bag valve is opened, gas from the ventilator passes into the bag from which it may be drawn freely by the patient in an unassisted manner. Electronic controls provide means for varying the proportion of breaths to be assisted by the ventilator to the breaths from the bag which, of course, are unassisted. The exhalation valve normally provided, is normally operatively connected to the ventilator in the usual way, when the device is in the assisted mode. However, during the unassisted mode, the exhalation valve is isolated from the rest of the circuit so that no pressure pulses be fed to the exhalation valve during this time. By utilizing the bag and bag valve, both assisted and unassisted breaths consist of gas from the ventilator with the same amount of humidity and oxygen components.

8 Claims, 8 Drawing Figures

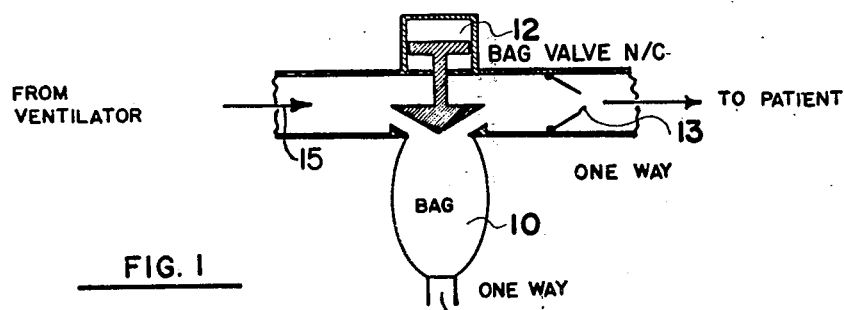
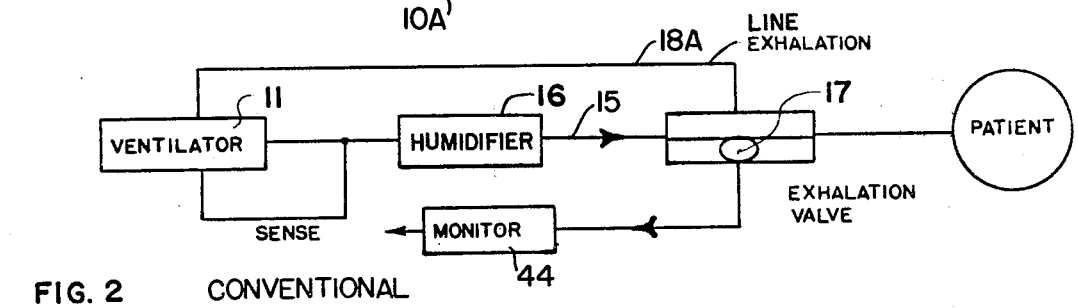
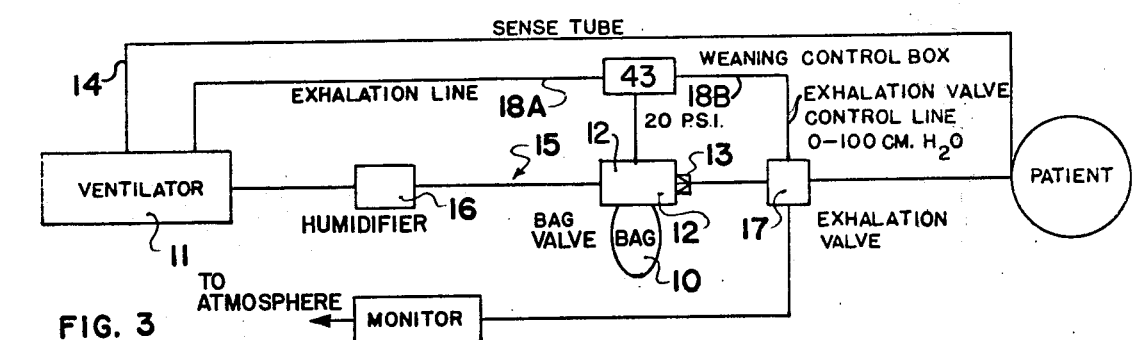
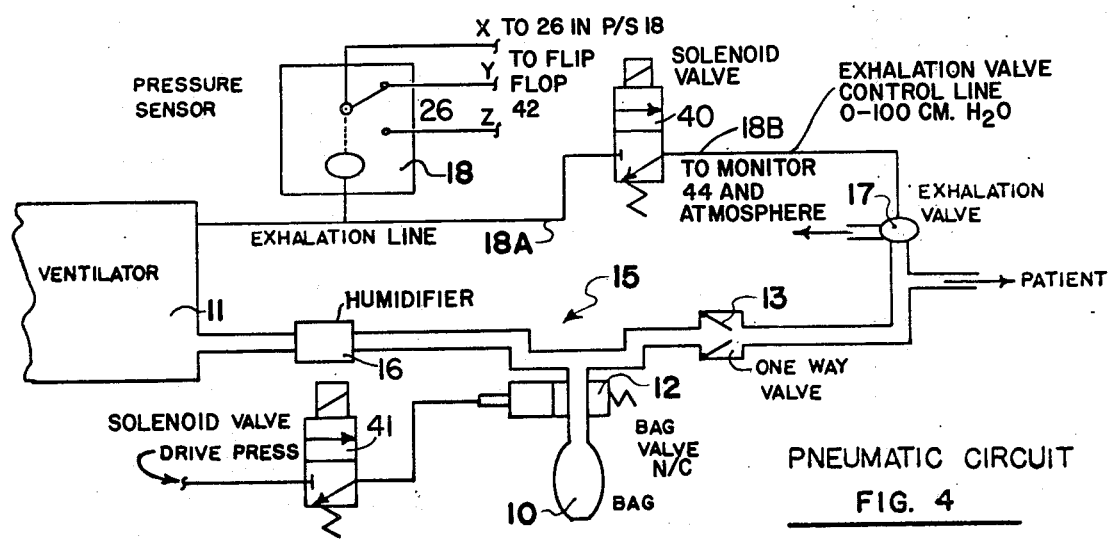

WEANER BLOCK DIAGRAM

POWER SUPPLY

LOGIC TIMING DIAGRAM

COUNTER DIAGRAM

METHOD AND APPARATUS FOR WEANING PATIENT FROM CONTINUOUS MECHANICAL VENTILATION

BACKGROUND OF THE INVENTION

This invention relates to new and useful improvements in methods and apparatus for weaning patients from continuous mechanical ventilators.

There are two methods to wean a patient with ventilatory failure away from continuous mechanical ventilation. The oldest method involves simply taking the patient off the ventilator for increasing periods. While off the ventilator, oxygen and humidity to the patient is provided by a heated nebulizer requiring a second ventilatory circuit and equipment.

A newer method called intermittent mandatory ventilation (IMV) essentially combines the action of both circuits and while allowing the patient to breathe at his own rate and depth, occasionally at a preset rate superimposes large mandatory breaths from the ventilator. I.M.V. is useful in patients with airways obstruction or neurological problems but requires complex tubing connections, there is assynchrony between patient and ventilator and there is difficulty in monitoring rate and volume of each breath. A variation of this method of weaning is synchronized I.M.V. (S.I.M.V.) whereby the mandatory large breath is synchronized to the patient's inspiratory effort.

An ideal method of weaning should allow synchrony between the patterns of breathing of the patient and ventilator, it should use the ventilator to provide oxygen and humidity for both assisted and unassisted breaths, and it should allow monitoring of the breathing pattern that results.

SUMMARY OF THE INVENTION

The system we have devised uses a bag and valve and an electronic and pneumatic controller connected to the conventional ventilator to provide for a variable proportion of breaths to be assisted (controlled) by the ventilator while the rest are due solely to patient effort. The system described herein is an improved method of S.I.M.V.

One aspect of the invention is to provide a continuous mechanical ventilation system which includes a conventional ventilator, a pneumatic connection between said ventilator and the patient attached thereto, an exhalation valve and an exhalation valve control line between the ventilator and the valve; means to provide assisted breaths from the ventilator to the patient when in an assisted mode, means to bypass breaths from said ventilator whereby the patient breathes unassisted breaths when in an unassisted mode, means to allow monitoring of the exhaled breaths of the patient, and means operatively connected to the system whereby the ratio of assisted and unassisted breaths may be varied within limits.

Another aspect of the invention is to provide a device in which the gas or air utilized by the patient, contains the same components whether the device is in the assisted or unassisted mode.

Another object of the invention is to provide a device of the character herewithin described in which the ratio of assisted breaths to unassisted breaths may be varied within limits.

A still further object of the invention is to provide a device of the character herewithin described which is relatively simple in construction, economical in manufacture, easy to attach to any ventilator and otherwise well suited to the purpose for which it is designed.

With the foregoing objects in view, and other such objects and advantages as will become apparent to those skilled in the art to which this invention relates as this specification proceeds, our invention consists essentially in the arrangement and construction of parts all as hereinafter more particularly described, reference being had to the accompanying drawings in which:

DESCRIPTION OF THE DRAWINGS

FIG. 1 is a schematic diagram of the bag and valve portion of the pneumatic circuit.

FIG. 2 is an overall schematic diagram of a ventilator as normally used.

FIG. 3 is an overall schematic diagram for a ventilator with the weaner circuitry added thereto.

FIG. 4 is a schematic diagram of the pneumatic circuit.

In the drawings like characters of reference indicate corresponding parts in the different figures.

DETAILED DESCRIPTION

Figure 5:
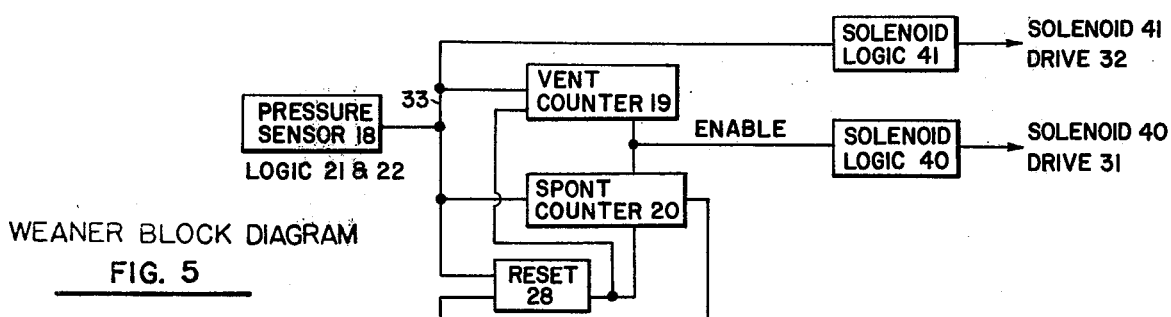
FIG. 5 is a block diagram of the weaner circuitry.

Proceeding therefore to describe the invention in detail, reference should be made to the drawings in which the pneumatic circuit consists, in this embodiment of a 3 liter bag 10 into which a ventilator 11 may deliver gas when the patient's breath is to be spontaneous or unassisted. The bag can be closed off with a low resistance powered valve 12 when the patient is to receive an assisted breath from the ventilator 11. These two modes are called "unassisted" (or "spontaneous") and "assisted". A one-way valve 13 downstream from the bag prevents exhaled gas from going into the bag.

A control box 43, that the ventilator senses or controls, counts each breath. Switches 37 and 38 allow the ratio of "assisted" to "unassisted" breaths to be varied from 9/1 to 1/40, in a preferred embodiment. The patient may thus receive, although other ratios may be chosen, 90% of his ventilation under power from the ventilator or, at the end of his weaning, may receive only one breath in forty. (Not all ratios from 9/1 to 1/40 are required, however.) The control box contains solenoid valves 41 and 40 which control the bag-valve 12 and the exhalation valve 17 attached to the ventilator 11.

Ventilation is actually sensed by the ventilator 11 which may be any assist-type or triggered ventilator. It is important that even small inspiratory efforts are sensed, thus the sense tube 14 in the pneumatic circuit should be connected close to the patient. When the ventilator trips "on", the beginning of the development of pressure in the exhalation line 18A is sensed by a pressure sensor 18 which drives switch 26 in the control box and depending on the state of the counter, the breath is controlled to be either assisted or spontaneous (unassisted).

The patient receives exactly the same oxygen concentration during unassisted or assisted breaths. Humidity is provided by the heated bypass humidifier 16 of the ventilator. All the gas leaving through the exhalation valve 17 is normally exhaled volume and therefor can be monitored easily. In case of a failure in either the ventilator or the weaner system. An external monitor 44 will produce an alarm.

The powered bag-valve 12 should be in the closed position normally and should open under power. Failure of the control box would produce the fail-safe result of the patient's going back on assisted ventilation.

Provision is made for the weaner to function whether or not the ventilator is set to provide a positive end expiratory pressure (PEEP) feature.

The overall schematics are shown in FIG. 2 for a ventilator as normally used, and in FIG. 3 with our weaning circuitry added.

CIRCUIT DESCRIPTIONS

1. Pneumatic Circuit (see FIG. 4)

A pressure sensor 18 generates logic signals corresponding to patient inspiration and expiration. It will sense positive pressure on the exhalation valve control line 18A from the respirator or ventilator 11. The trip point, nominally of the order of 20 cm $H_2O$, was chosen so that the respirator 11 can operate with positive and expiration pressure (PEEP), if required, during the "ventilation" or "assisted" mode. (Nominal values of PEEP are usually less than 15 cm $H_2O$, so exhalation control pressure is chosen to be greater in order to achieve positive shutoff). Solenoid valve 40 isolates the exhalation valve 17 from any pressure from the respirator 11 and connects it to atmosphere or to a PEEP pressure. During the "assisted" mode this solenoid 40 is energized and the exhalation valve 17 operates normally. During the "unassisted" mode the exhalation valve 17 is isolated from the rest of the circuit. This was done so that no pressure can remain on the exhalation valve control line 18B during "unassisted" time. (The sources of pressure are positive end expiration pressure and, if selected exhalation drive pressure.)

The bag valve 12 should be of the normally closed type in order to be fail safe. During "assisted" time this valve offers a resistance of <0.5 cm $H_2O/L/S$ in the line 15 from the respirator to the patient. During "unassisted" time this valve offers a resistance of <0.5 cm $H_2O/L/S$ between the bag 10 and the patient.

The bag 10 is relatively flaccid and is formed from a flexible material such as rubber, synthetic plastic or the like. The one-way valve 13 acts as a resistance to flow to the patient so that when the bag valve 12 is open, gas from the ventilator 11 normally passes to the bag 10 and the patient draws air from the bag during the "unassisted" time or mode. When the bag valve 12 is closed, the patient receives air from the ventilator during this "assisted" time or mode. It will be noted in both the "assisted" and "unassisted" modes, the gas or air is the same with the same humidity and oxygen content inasmuch as it is derived from the ventilator in both cases.

2. Weaner Block and Timing Diagram (See FIGS. 5 and 7)

The pressure sensor 18 and logic generates a logic signal 33 every time the respirator exhalation drive line pressure exceeds 20 cm $H_2O$, as an example. i.e. for each vent or spont breath. All breaths are counted when they end.

After switch 28 is reset which starts the cycle, the vent counter is enabled. The spont counter is not enabled. The system is put in the vent mode by the action of solenoid drives 30 and 31. Vent breaths occur until the number equals that selected by the vent counter. The end of the last vent breath enables the spont counter. The vent counter is now not enabled. The system is put in the spont mode by the action of solenoid drives 30 and 31. Spont breaths occur until the number equals that selected by the spont counter. The end of the last spont breath creates a reset enable. At the initiation of the following breath, a reset is generated. The cycle now starts again.

The logic blocks 21 and 22 are composed of the switches, gates, and associated circuit components which are connected with the counters 19 and 20 to form an electronic logic circuit as discussed in detail below.

Figure 6:
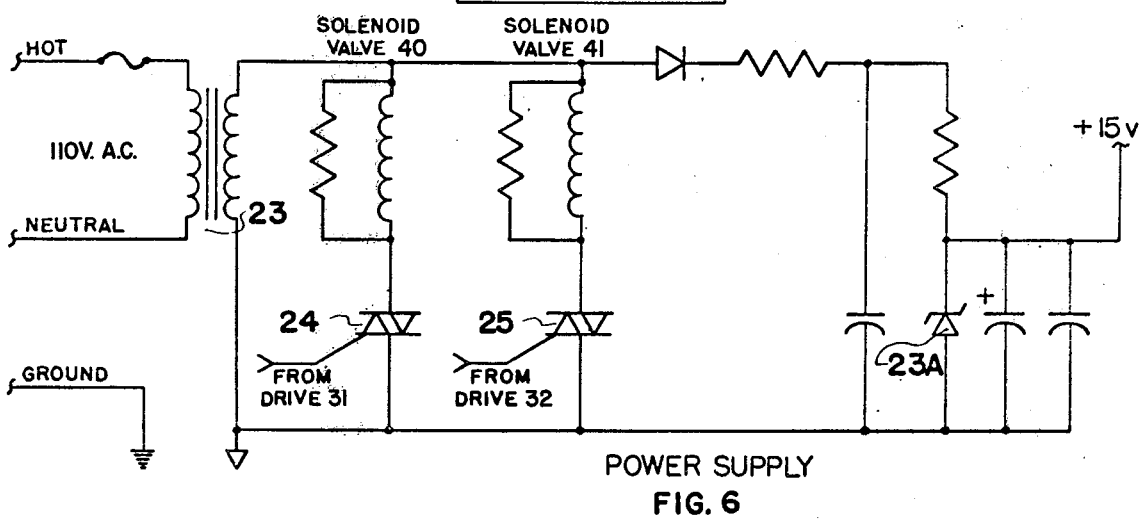
FIG. 6 is a circuit diagram of the power supply.

3. Circuit Diagram (See FIG. 8 and Power Supply diagram FIG. 6)

Figure 8:
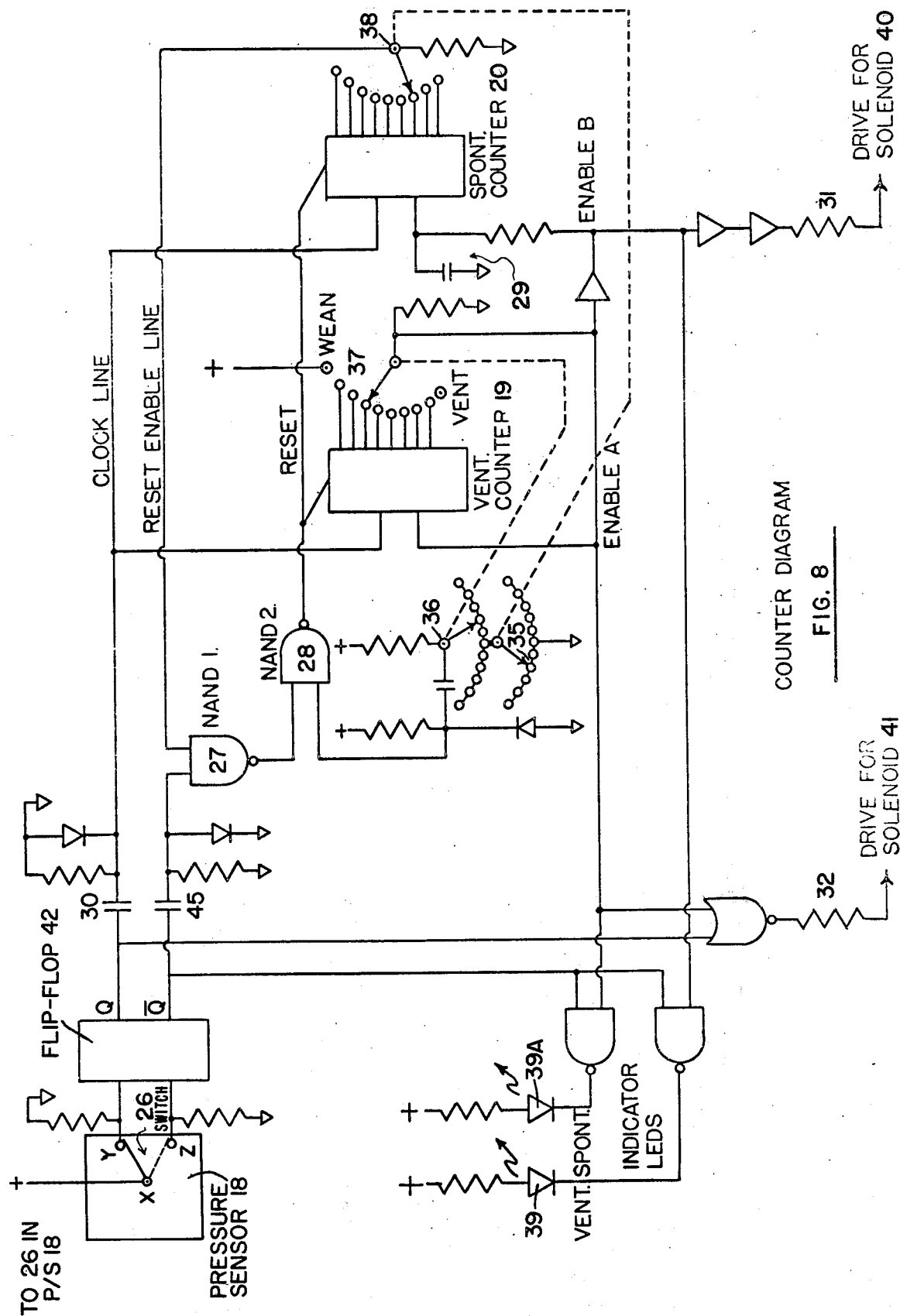
FIG. 8 is a circuit diagram of the counter portion.

In a preferred embodiment, all of the circuitry is solid state with CMOS circuits used for the logic. The solenoid valves 40 and 41 run from 110 V A.C. supplied from an isolation transformer 23. The regulated supply comprising +15 V Zener diode 23A and associated components, for the logic is also derived from this transformer. Equivalent controls of other types are within the scope of this invention. The solenoids 40 and 41 are activated by triacs 24 and 25, respectively, which are controlled by 15 volt logic signals 31 and 32 from the control logic (FIG. 8).

The pressure sensor 18 may be a diaphragm which moves under pressure to activate a micro switch 26. This switch (single pole double throw) is buffered with a flip-flop 42 to produce a no-bounce logic signals. Both outputs Q and $\bar{Q}$ of the flip-flop are used in the logic. Because breaths [1] are counted just as they end, and the reset pulse is generated at the beginning of a breath, the start of a cycle is sometimes during a breath. After the start of a cycle when that breath is finished, the positive going output of the flip-flop is differentiated 34 by the resistor-diode-capacitor combination 30 and applied to the clock input of both counters 19 and 20, which are made up of 4017 decade counters [2].

[1] To avoid confusion as to whether a patient inspires or the respirator expires, we speak of the respirator delivering air or just breaths. Note that the term "unassisted breath" is used interchangeably with "spontaneous breath" or SPONT. Equally, "assisted breath" is equivalent to "ventilated breath" or VENT.
[2] The diagram shows nine switch positions since it was felt that more than nine would be too cluttered for simple operation. Additional steps can, of course, be added, as may be useful for a given application. The value of each step is taken from the appropriate output of the counters 19 and 20.

Figure 7:
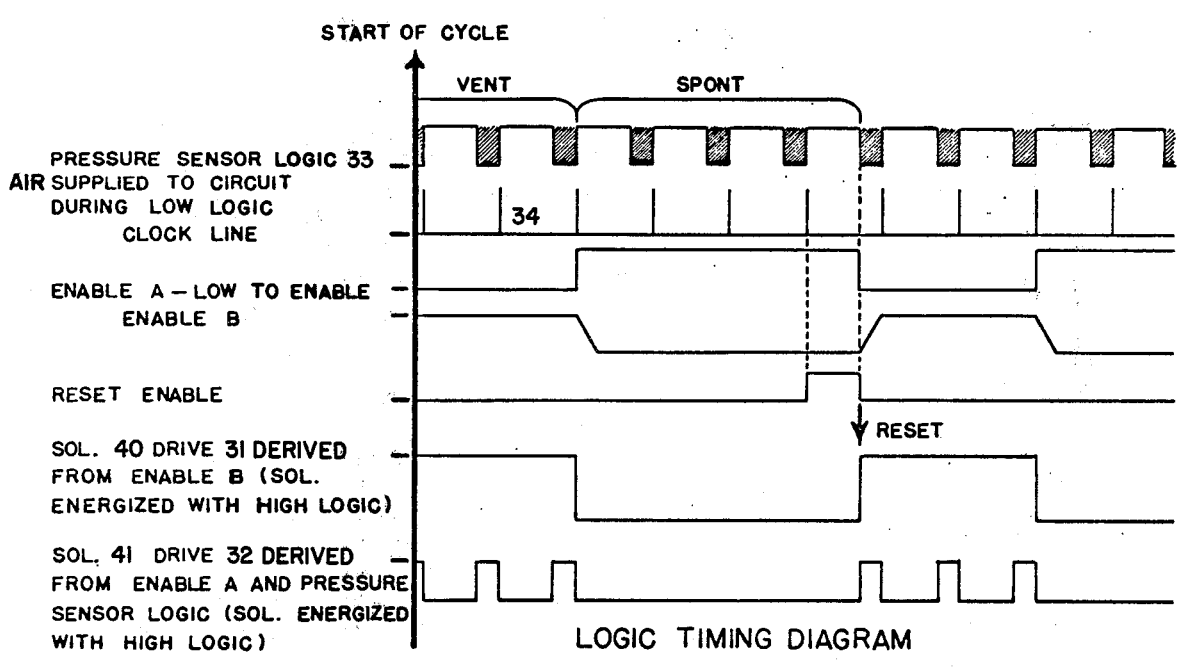
FIG. 7 is a logic timing diagram.

The vent counter 19 is enabled and will count breaths until the selected output goes high (See FIG. 7). During this time solenoid 40 is continuously energized and solenoid 41 is energized 32 when the respirator is delivering air [3]. On the switch 37, which selects the number of assisted breaths, there are two additional positions. One is "vent assist" which holds the weaner in the "assisted" mode, the other is "wean" which holds it in the spont mode. When the selected output of the "vent" counter goes high it will disable itself. The inverse of this signal is used to enable the spont counter 20. There is an R.C. delay 29 in the enable circuit to the spont counter 20 so that it doesn't count the last assisted breath. The following breaths will now be counted on the spont counter. During this time solenoids 40 and 41 are not activated. When the selected output of the spont counter 20 goes high NAND 1 (27) is enabled. This happens at the end of the last unassisted breath. At the beginning of the next breath when the $\bar{Q}$ output of the flip-flop 42 goes positive it is differentiated through network 45 and is gated through NAND 1 and through NAND 2 (28) and resets both counters to zero. This will start the whole cycle over again.

(3) The term "solenoid" is used here as a short form of "solenoid powered pneumatic valve".

Also included in the logic are switch decks 35 and 36, one on each of the spont switch 38 and vent switch 37. Whenever either switch 37 or 38 is changed these additional decks 35 and 36 will produce a reset pulse. This prevents the weaner from going through an illogical sequence. For example, without this feature: if the spont counter switch 38 were set on 3 breaths and the spont counter 20 counted to 2, changing counter switch 20 to "1", passing through "2", would not result in a reset because the end of a breath must occur to generate the reset logic. The spont counter would then have to count through its whole sequence resulting in far too many unassisted breaths having to be generated by the patient.

LED (light emitting diodes) indicators 39 and 39A are included to indicate to the operator what state the weaner is in. The appropriate LED lights when the respirator 11 is delivering air to indicate if the breath is "assisted" or "unassisted".

47 is a box or container within which the bag may operate. The purpose of this box or container is to provide a positive pressure around the bag so that there is no resistance in breathing from the bag when there is positive end expiratory pressure (P.E.E.P.) in the breathing circuit.

Pressure in the box is maintained at the same level as the end expiratory pressure by means of a pressure line 48 which connects the box 47 to the line from the ventilator to the patient, immediately downstream from the one way valve 13.

The breath counter idea herein described is not the only way in which the breathing bag concept can be utilized. It is also appropriate for use with the "time window" and related approaches (as typified by mechanizations in the Bennett MA-1 and Monaghan 225 ventilators).

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. In a conventional ventilator which supplies assisted or unassisted breaths to a patient including a pneumatic connection extending from said ventilator, an exhalation valve operatively connected to said pneumatic connection, patient connection means extending from said exhalation valve, an exhalation valve control line operatively connected between the ventilator and the exhalation valve and means operatively connected to said exhalation valve to monitor exhaled breaths; the improvement comprising an attachment, said attachment comprising means to provide assisted breaths from the ventilator when in an "assisted" mode, means to by-pass breaths from said ventilator when in an "unassisted" mode and means operatively connected to the means to monitor the exhaled breaths whereby the ratio of "assisted" and "unassisted" breaths may be varied within limits, said means to provide "unassisted" breaths including a low resistance bag valve in said pneumatic connection, a bag connected to the bag valve, a one-way valve operatively connected between said bag and said exhalation valve providing one-way flow from said bag to said exhalation valve, the operation of said ventilator including means to open and close said bag valve whereby breaths from said ventilator are conveyed directly to said patient connection means when said bag valve is closed and said ventilator is in the "assisted" mode, and to the bag and thence to said patient connection means as required, when said bag valve is open and said ventilator is in the "unassisted" mode, said means operatively connected to said means to monitor the exhaled breaths whereby the ratio of "assisted" and "unassisted" breaths may be varied within limits, including a pressure sensor in said exhalation valve control line, a signal generator operatively connected to said pressure sensor and operated thereby each time the exhalation pressure within said control line exceeds a predetermined pressure, assisted breath counter means, and unassisted breath counter means, means operatively connecting said signal generator to said assisted breath counter means when in the "assisted" mode and to said unassisted breath counter means when in the "unassisted" mode, means to vary the ratio of connection of said signal generator to said assisted and unassisted counter means, a bag valve solenoid operatively connected to said bag valve and means to operate said bag valve solenoid operatively extending from said unassisted breath counter means to said solenoid.

2. The invention according to claim 1 in which said bag valve is normally closed thereby acting as a fail safe mechanism and placing the system in the "assisted" breath mode.

3. The invention according to claim 1 in which said means operatively connected to said means to monitor the exhaled breaths to vary the ratio of assisted and unassisted breaths also includes an exhalation valve solenoid operatively connected between said exhalation valve and said exhalation valve control line, and means to operate said exhalation valve solenoid operatively connected between said assisted breath counter means and said solenoid whereby said exhalation valve control line is open between said ventilator and said exhalation valve and said valve operates normally when said ventilator is in the "assisted" mode and said exhalation valve control line is closed between said ventilator and said exhalation valve when said ventilator is in the "unassisted" mode thereby isolating said exhalation valve from the exhalation valve control line.

4. The invention according to claim 3 in which said bag valve is normally closed thereby acting as a fail safe mechanism and placing the system in the "assisted" breath mode.

5. In a continuous mechanical ventilation system which includes a conventional ventilator which supplies assisted and unassisted breaths to a patient, a pneumatic line operatively extending from said ventilator, an exhalation valve operatively connected to said pneumatic line and an exhalation valve control line extending between said ventilator and said exhalation valve, patient connection means extending from said exhalation valve; means to assist in weaning patients away from said ventilator, said means including a bag valve in the pneumatic line between said ventilator and said exhalation valve, a bag connected to said bag valve, a one-way valve operatively connected between said bag and said exhalation valve providing one-way flow from said bag valve to said exhalation valve, means to actuate said bag valve whereby breaths from said ventilator are conveyed to said patient connection means when said bag valve is closed and said ventilator is in the "assisted" mode and to said bag and thence to said patient connection means as required, when said bag valve is open and said ventilator is in the "unassisted" mode, and means operatively connected to said means to actuate said bag valve, to vary the ratio of the number of breaths directly to said patient connection means and the number of breaths to said patient connection means via said bag, within limits, said means to vary the ratio of the number of breaths directly to said patient connection means and via said bag, including a pressure sensor in said exhalation valve control line, a signal generator operatively connected to said pressure sensor and operated thereby, each time the exhalation pressure within said control line exceeds a predetermined pressure, assisted breath counter means, unassisted breath counter means, means operatively connecting said signal generator to said assisted breath counter means when in the "assisted" breath mode and to said unassisted breath counter means when in the "unassisted" mode, means to vary the ratio of connection of said signal generator to said assisted and unassisted counter means, a bag valve solenoid operatively connected to said valve and means to operate said bag valve solenoid extending from said unassisted breath counter means to said solenoid.

6. The invention according to claim 5 in which said bag valve is normally closed thereby acting as a fail safe mechanism and placing the system in the "assisted" breath mode.

7. The invention according to claim 5 which also includes an exhalation valve solenoid operatively connected between exhalation valve and said exhalation valve control line, and means to operate said exhalation valve solenoid operatively connected between said assisted breath counter means and said solenoid whereby said exhalation valve control line is open between said ventilator and said exhalation valve and said valve operates normally when said ventilator is in the "assisted" mode and said exhalation valve control line is closed between said ventilator and said exhalation valve when said ventilator is in the "unassisted" mode thereby isolating said exhalation valve from the exhalation valve control line.

8. The invention according to 7 in which said bag valve is normally closed thereby acting as a fail safe mechanism and placing the ventilator in the "assisted" breath mode.

* * * * *